United States Patent [19]

Schnabel

[11] 4,239,902

[45] Dec. 16, 1980

[54] N-CARBOXYACYLAMINOACID ESTERS, PROCESSES FOR THEIR PRODUCTION AND THEIR DIAGNOSTIC USE

[75] Inventor: Eugen Schnabel, Wuppertal, Fed. Rep. of Germany

[73] Assignee: Bayer Aktiengesellschaft, Leverkusen, Fed. Rep. of Germany

[21] Appl. No.: 18,701

[22] Filed: Mar. 8, 1979

[30] Foreign Application Priority Data

Apr. 11, 1978 [DE] Fed. Rep. of Germany ....... 2815555

[51] Int. Cl.$^3$ ..................... C07C 101/08; G01N 31/00
[52] U.S. Cl. ........................... 560/41; 260/326.14 A; 260/326.14 T; 424/12; 560/39; 560/40
[58] Field of Search ............................ 560/41, 40, 39; 260/326.14 A, 326.14 T

[56] References Cited

U.S. PATENT DOCUMENTS 4,105,789  8/1978  Ondetti et al. .......................... 560/41

OTHER PUBLICATIONS

Cushman et al., Biochemistry, 16(25), pp. 5484–5491, (1977).
Starkey et al., Biochem. J., 155, 273 (1976).

*Primary Examiner*—Natalie Trousof
*Assistant Examiner*—G. T. Breitenstein
*Attorney, Agent, or Firm*—Sprung, Felfe, Horn, Lynch & Kramer

[57] ABSTRACT

The invention relates to N-carboxyacylaminoacid esters, a process for their production and their use as chromogenic substrates for the continuous and discontinuous determination of enzymes with a chymotrypsin-like specificity, in particular catheepsin G.

6 Claims, 2 Drawing Figures

N-CARBOXYACYLAMINOACID ESTERS, PROCESSES FOR THEIR PRODUCTION AND THEIR DIAGNOSTIC USE

The present invention relates to new carboxyacylaminoacid esters, to a process for their production and to their use as chromogenic substrates for continuous and discontinuous determination of enzymes with a chymotrypsin-like specificity, in particular cathepsin G.

It has already been disclosed that $\beta$-naphthyl esters of acetyl- and benzoyl-phenylalanine can be used for the determination of chymotrypsins, and in particular of cathepsin G, the chymotrypsin-like enzyme from granulocytes. [P. M. Starkey and A. J. Barrett, Biochem. J. 155, 273 (1976)]. The $\beta$-naphthol liberated is determined colorimetrically, after coupling with diazonium compounds. According to H. Fritz, F. Woitinas and E. Werle, H. S. Z. Physiol. Chem. 345, 168 (1966), the values thereby obtained for chymotrypsin in solutions with a high protein content are not reproducible. In addition, both substrates are very lipophilic and homogeneous solutions can scarcely be obtained, even by adding detergents. It is possible to use substrates which are more readily soluble in water, such as succinyl-L-phenylalanine p-nitroanilide [W. Nagel, F. Willig, W. Peschke and F. H. Schmidt, H. S. Z. Physiol. Chem. 340, 1 (1965)], glutaryl-L-phenylalanine p-nitroanilide [B. F. Erlanger, F. Edel and A. G. Cooper, Arch. Biochem. Biophys. 115, 206 (1966)] or glutaryl-diglycyl-L-phenylalanine $\beta$-naphthylamide [H. Rinderknecht and R. M. Fleming, Clin. Chim. Acta 59,139 (1975)] only in the case of the determination of chymotrypsin, because these substrates are not split by cathepsin G [P. M. Starkey and A. J. Barrett, Biochem. J. 155, 273 (1976)].

According to the present invention there are provided compounds which are N-carboxyacyl aminoacid esters of the general formula in which
X denotes a straight-chain $C_2$ to $C_4$ alkylene or alkenylene radical which is optionally substituted by $C_1$ to $C_4$ alkyl, or an optionally substituted o-phenylene radical,
Y denotes an optionally substituted phenyl or naphthyl radical and
Z denotes a phenyl or indolyl radical which is optionally substituted by hydroxyl.

The compounds of the invention are readily soluble in aqueous systems and are outstandingly suitable as substrates for the chymotrypsins and chymotrypsin-like enzymes, especially cathepsin G. The compounds of the invention preferably belong to the L-series, but they can also be in the racemic form.

Examples of suitable radicals X are ethylene, propylene, butylene or o-phenylene; examples of suitable radicals Y are $\alpha$-naphthyl, $\beta$-naphthyl, phenyl and 4-nitrophenyl; and examples of suitable radicals Z are phenyl, 4-hydroxyphenyl and $\beta$-indolyl.

Preferred compounds of the invention are succinyl-L-phenylalanine $\beta$-naphthyl ester, succinyl-L-phenylalanine 4-nitrophenyl ester, adipyl-L-phenylalanine $\beta$-naphthyl ester and adipyl-L-phenylalanine 4-nitrophenyl ester.

Figure 1:
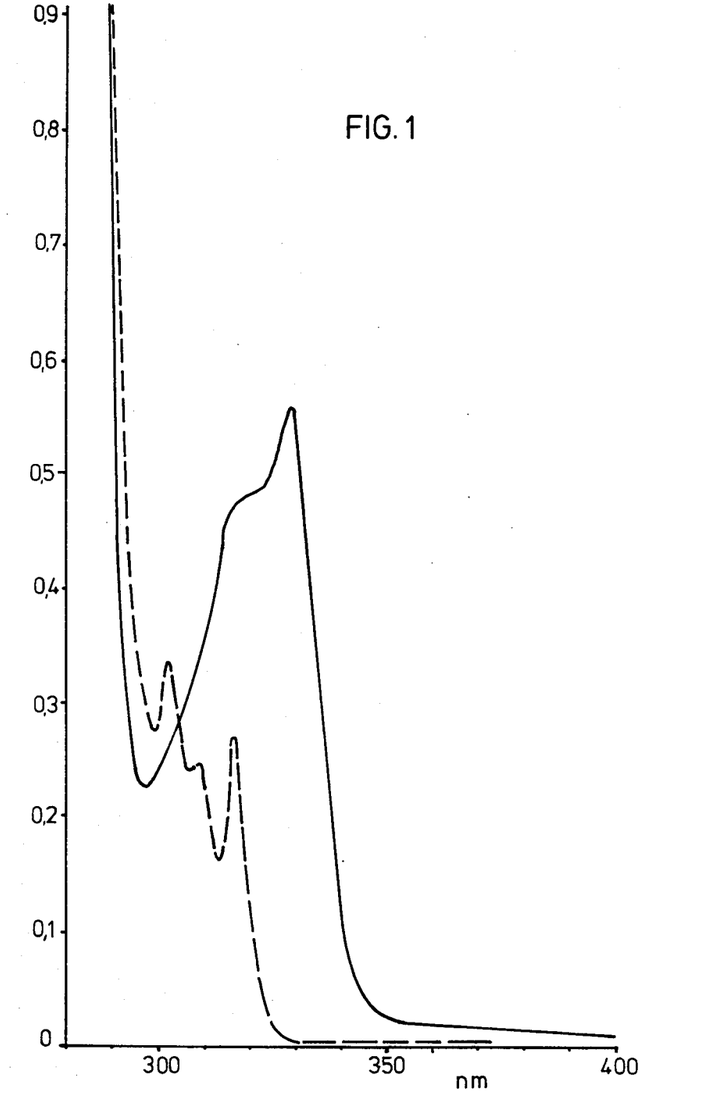
FIG. 1: | UV absorption spectrum of |
| - - - - | Succinyl-L-phenylalanine β-naphthyl ester, $10^{-3}$M in 0.25 M tris buffer of pH 7.2 ($E_{315} = 270$; $E_{302} = 325$) |
| ——— | β-Naphthol, $3.1 \cdot 10^{-4}$ M in 0.25 M tris buffer of pH 7.2 ($E_{329} = 1,790$) |
|

The activity of the specified enzymes can be determined not only by an end point method, after stopping the enzyme reaction and coupling the $\beta$-naphthol formed with diazonium compounds, as described in the case of the use of acetyl- or benzoyl-phenylalanine $\beta$-naphthyl ester, but it can also be determined continuously, according to the invention, with the aid of the increase in extinction, caused by liberation of the phenols and naphthols, at a wavelength at which the esters are virtually non-absorbing. As a comparison of the absorption spectra of succinyl-L-phenylalanine $\beta$-naphthyl ester and of $\beta$-naphthol in FIG. 1 shows the absorption maximum on splitting shifts to longer wavelengths, becoming more intense, and the molar extinction of $\beta$-naphthol at 329 nm in a 0.25 M tris-(hydroxymethyl)-aminomethane buffer of pH 7.2 is 1,790 $mol^{-1}.cm^{-1}$. Using this substrate, accurate determination of chymotrypsins and of cathepsin G is possible, even in solutions with a high protein content. The sensitivity of the test can be increased, as described for the end point method [H. A. Ravin, P. Bernstein and A. M. Seligman, J. Biol. Chem. 208, 1 (1954)], by coupling the $\beta$-naphthol with a diazonium compound after a given time and determining the very much higher extinction of the azo derivative. The difference between the extinction maxima of succinyl-L-phenylalanine p-nitrophenyl ester ($\lambda_{max}$270 nm) and p-nitrophenol ($\lambda_{max}$100 nm) is even greater. When succinyl-L-phenylalanine $\beta$-naphthyl ester is used as the substrate, the measurements are carried out at pH values between pH 6.5 and 8.5; below pH 6.5, the substrate is sparingly soluble in aqueous systems, and above pH 8.5, spontaneous hydrolysis of the activated esters proceeds so rapidly that the determinations become inaccurate. If appropriate, the test solutions can contain additives, such as detergents and/or organic solvents. Examples of suitable detergents are polyethylene glycol fatty alcohol ethers, for example polyethylene glycol containing about 20 ethylene oxide units, etherified with lauryl alcohol, or derivatives of cholic acids. Examples of suitable organic solvents are dimethylsulphoxide, dimethylformamide, dimethylacetamide or hexamethylphosphoric acid triamide.

The substrates according to the invention are very specific for the chymotrypsins and for cathepsin G. Table 1 indicates the ease of splitting succinyl-L-phenyl-alanine $\beta$-naphthyl ester by various proteases, relative to $\alpha$-chymotrypsin (100%).

The Michaelis constants of $\alpha$-chymotrypsin and cathepsin G and succinyl-L-phenylalanine $\beta$-naphthyl ester at 25° C. in the above 0.25 M tris-(hydroxymethyl)-aminomethane/hydrochloric acid buffer of pH 7.2 were determined as $4.2 \cdot 10^{-4}$ mol/l and $4.5 \cdot 10^{-4}$ mol/l respectively, by the method of H. Lineweaver and D. Burk [J. Amer. Chem. Soc. 56,658 (1934)]. The corresponding values for the substrate adipyl-L-phenylalanine $\beta$-naphthyl ester were found to be $6.4 \cdot 10^{-4}$ mol/l and $7.2 \cdot 10^{-4}$ mol/l respectively.

Figure 2:
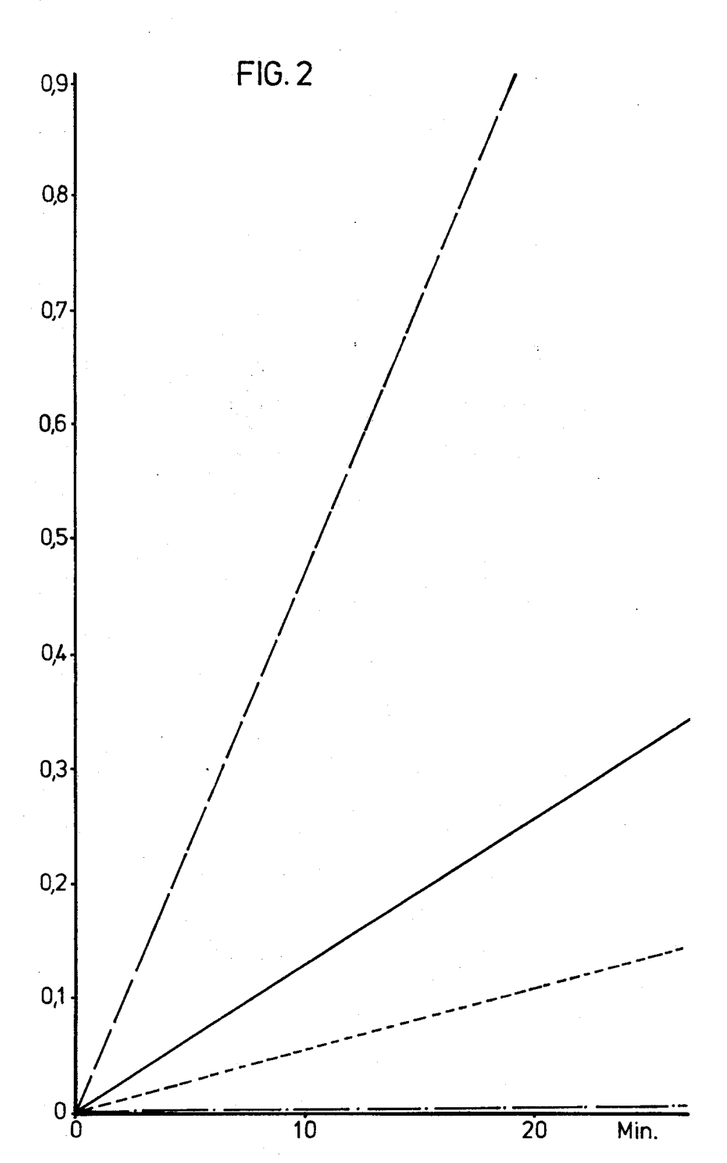
FIG. 2: | Splitting of succinyl-L-phenylalanine β-naphthyl ester and glutaryl-L-phenylalanine p-nitroanilide by chymotrypsin |
| - - - - | $10^{-3}$ M solution of succinyl-L-phenylalanine β-naphthyl ester (2.5 ml) with $8 \cdot 10^{-4}$ mg of α-chymotrypsin |
| · · · · | Spontaneous hydrolysis of succinyl-L-phenylalanine β-naphthyl ester |
| ——— | $10^{-3}$ M solution of glutaryl-L-phenylalanine p-nitroanilide (2.5 ml) with $8 \cdot 10^{-2}$ mg of α-chymotrypsin |
| -·-·- | $10^{-3}$ M solution of glutaryl-L-phenylalanine p-nitroanilide (2.5 ml) with $8 \cdot 10^{-4}$ mg of α-chymotrypsin |

The increases in extinction resulting from the splitting of succinyl-L-phenylalanine $\beta$-naphthyl ester according to the invention and of glutaryl-L-phenylalanine p-nitroanilide, which is known, are shown in FIG. 2. Taking into consideration that the molar extinction coefficient of p-nitroaniline at 8,800 $mol^{-1}.cm^{-1}$ is greater than that of $\beta$-naphthol by a factor of almost 5, it is found that the splitting of the substrate according to the invention is faster by a factor of at least 1,000. The detection limit of chymotrypsin is thus increased by a factor of at least 100. With regard to the high specificity of the compounds according to the invention as substrates for chymotrypsin and chymotrypsin-like enzymes (compare Table 1), these derivatives represent an advance in enzyme chemistry, in particular for the determination of enzymes.

With regard to the pathogenetic significance of neutrophilic proteases, and in particular of cathepsin G [A. Janoff, Ann. Rev. Med. 23, 177 (1972)], the substrates according to the invention are valuable diagnostic auxiliaries.

The N-carboxyacyl-aminoacid esters according to the invention are obtained when the aminoacid esters of the general formula II in which Z and Y have the abovementioned meaning, are reacted with dicarboxylic acid anhydrides of the general formula III wherein X has the above-mentioned meaning, at pH values between 2 and 7, preferably at pH 4–6, in suitable solvents.

Suitable solvents for this reaction which may be mentioned are, in particular, acetone, acetonitrile, chloroalkanes having 1 to 4 carbon atoms (e.g. chloroform, dichloroethane, etc.) dioxane, dimethylformamide, glacial acetic acid, tetrahydrofurane and water. They can also be used as mixtures. The pH value of the reaction solutions is kept in the desired range either by adding baes or using buffer solutions; in certain circumstances, the ester hydrochlorides can be employed for the reactions, without adding bases.

The reactions are preferably carried out at temperatures between −10° C. and +50° C., preferably at 0°–10° C., the reaction solutions first being cooled and then being allowed to warm.

Suitable cyclic dicarboxylic acid anhydrides which may be mentioned are, in particular, the anhydrides of succinic acid and of phthalic acid. They can optionally also carry additional substituents.

It has indeed already been disclosed that cyclic anhydrides of dicarboxylic acids react with aminoacids and their derivatives, such as the free alkyl esters [C. Berse, L. Piche, L. Lachance and G. Laflamme, J. org. Chem. 27, 3489 (1962); and B. Helferich and W. Wesemann, Chem. Ber. 100, 421 (1967)] or optionally substituted amides, in particular the p-nitronalides [B. F. Erlanger, F. Edel and A. G. Cooper, Arch. Biochem. Biophys. 115, 206 (1966)], preferably under alkaline conditions. Phenyl esters and naphthyl esters of aminoacids, as so-called "activated esters" [G. Wendlberger in E. Müller (editor), Houben-Weyl, Methoden der Organischen Chemie (Methods of Organic Chemistry), 4th edition 1974, Volume 15/2, Georg Thieme Verlag, Stuttgart], have not hitherto been reacted with cyclic dicarboxylic acid anhydrides. It was to be assumed that, in reactions with dicarboxylic acid anhydrides under the customary reaction conditions, the activated aminoacid esters would be split by reaction with their own amino group, or by hydrolysis in the presence of water. Surprisingly, it has now been found that the N-carboxyacyl compounds according to the invention are obtained in high yields in the reactions with the hydrochlorides of the activated aminoacid esters in an acid medium.

Alternatively, however, the N-carboxyacylaminoacid esters according to the invention can also be obtained by acidolytic splitting of the ω-tert.-butyl esters of the N-carboxyacylaminoacid esters, of the formula (IV)

in which X, Y and Z have the above-mentioned meaning.

Examples of acids which are suitable for the acidolysis are mineral acids or their solutions in, preferably, anhydrous organic solvents, such as ethyl ether, ethyl acetate, tetrahydrofurane, dioxane, glacial acetic acid or methanol. The acidolytic splitting reactions are carried out at temperatures between −10° C. and +50° C., preferably at 0°–25° C., and if appropriate under nitrogen.

The starting compounds (IV) required for the acidolysis are obtained by reacting activated derivatives of mono-tert.-butyl esters of the corresponding dicarboxylic acids with aminoacids, which can optionally be silylated, or aminoacid alkyl esters and then, after freeing the carboxyl group of the aminoacids and appropriate activation, reacting the products with the phenols or naphthols.

The compounds of the formula (IV) are also obtained by reacting monoactivated derivatives of dicarboxylic acids, the second carboxyl group of which is free, with aminoacid esters to give the N-carboxyacylaminoacid esters, and, after protecting the ω-carboxyl group and after deblocking the aminoacid carboxyl group, as described above, converting these products into the mono-tert.-butyl esters of the carboxyacylaminoacid-phenyl esters or -naphthyl esters.

The following examples are illustrative but not limitative of the invention.

EXAMPLE 1: Succinyl-L-phenylalanine β-naphthyl ester (a) tert.-Butoxycarbonyl-L-phenylalanine β-naphthyl ester 6.2 g of dicyclohexylcarbodiimide are added to a solution of 7.8 g of tert.-butyoxycarbonyl-L-phenylalanine and 5.3 g of β-naphthol in 50 ml of absolute tetrahydrofurane at 0° C. and the reaction mixture was kept at 4° C. for 12 hours. The dicyclohexylurea which had precipitated was then separated off by filtration and the filtrate was evaporated to dryness in vacuo. The crystalline residue was recrystallised twice from ethyl acetate/cyclohexane and finally from acetonitrile. 8.5 g (73% of theory) of melting point 118°–119° C. were obtained.

(b) L-Phenylalanine β-naphthyl ester hydrochloride 8.6 g of the compound prepared (according to 1a) were dissolved in 75 ml of absolute dioxane. 100 ml of 5 N ethereal HCl and 5 ml of trifluoracetic acid are added to this solution. The mixture was stirred at 20° C. for 3 hours and the hydrochloride was finally precipitated quantitatively by adding 100 ml of diisopropyl ether and 100 ml of cyclohexane to the reaction solution. On filtration, 6.8 g (94% of theory) of colourless crystals of melting point 219°–221° C. were obtained; melting point after recrystallisation from acetonitrile: 221°–222° C.

(c) Succinyl-L-phenylalanine β-naphthyl ester 10 ml of water were added to a suspension of 3.3 g of the compound obtained according to 1(b) and 1 g of succinic anhydride in 50 ml of acetonitrile at 4° C., and finally 4 N sodium hydroxide solution was added, whilst cooling further and stirring, until a pH of 5.0 was reached. After 20 minutes whilst maintaining this pH value, 2 g of succinic anhydride were introduced in portions at intervals of 10 minutes each, whilst stirring. 1 hour after the last addition, the reaction solution was concentrated in vacuo down to a volume of about 20 ml and 150 ml of ethyl acetate were then added. The solution was then extracted with 20 ml of 2 N suphuric acid and a further five times with 50 ml of warm water each time, and finally with 50 ml of hot water. The ethyl acetate was then distilled off in vacuo and the crystalline residue was recrystallised three times from acetonitrile. Yield: 3.44 g (88% of theory) of melting point 146°–147° C.

EXAMPLE 2: Adipyl-L-phenylalanine β-naphthyl ester (a) Adipic acid mono-p-nitrophenyl ester 28 g of finely powdered p-nitrophenol were added to 25.6 g of adipic anhydride and the mixture was stirred at room temperature overnight, whereupon the contents of the flask solidified. The mass was melted, whilst stirring, and the melt was dissolved in 350 ml of ethyl acetate. The solution was extracted several times with water and the ethyl acetate was distilled off in vacuo. The residue was recrystallised three times from acetonitrile. Yield: 45.2 g (85% of theory) of melting point 104°–105° C.

(b) Adipyl-L-phenylalanine benzyl ester 16.5 g of N-trimethylsiliyl-L-phenylalanine benzyl ester and 13.5 g of adipic acid mono-p-nitrophenyl ester were dissolved in 30 ml of absolute dioxane and this solution was kept at room temperature for 24 hours. The mixture was then warmed at about 60° C. for 5 hours and the dioxane was distilled off in vacuo. The residue was dissolved in 150 ml of ethyl acetate and the solution was extracted several times with 30 ml of 2 N sulphuric acid each time, and finally with water. After distilling off the ethyl acetate in vacuo, a yellowish syrup was obtained. In order to separate off the p-nitrophenol, the syrup was chromatographed on a packed column containing aluminium oxide, ¾ of which was neutral and ¼ of which was basic, using cyclohexane as the solvent. On concentrating the colourless eluates containing the substance, 17.8 g (93% of theory) of syrupy substance with a $R_f$ value of 0.90 in chloroform:methanol:ethyl acetate 190:10:6 (by volume) were obtained.

(c) N-tert.-butyl-adipyl-L-phenylalanine benzyl ester 0.1 ml of concentrated sulphuric acid and 75 ml of isobutylene were added to a solution of 10 g of the substance obtained according to 2b) in 50 ml of methylene chloride. The reaction mixture was kept in a closed vessel at 20° C. for 4 days, the vessel being shaken occasionally.

1 ml of triethylamine was then added and the reaction mixture was subsequently extracted several times with a 5 percent strength sodium bicarbonate solution and finally with water. After distilling off the isobutylene and the methylene chloride, the syrupy residue was dissolved in 25 ml of diisopropyl ether and the solution was chromatographed on a packed column containing neutral aluminium oxide and, in the upper quarter, basic aluminium oxide using diisopropyl ether, as described in 2(b). The eluates containing the desired substance were combined and the solvents were distilled off in vacuo. 10.2 g (86% of theory) of a colourless syrup were thus obtained; $[\alpha]_D^{20}: -9.3°$ (c=1, in dimethylformamide).

(d) tert.-Butyl-adipyl-L-phenylalanine

After adding palladium black, freshly prepared from 1 g of palladium chloride, a slow stream of hydrogen was allowed to bubble through a solution of 8.8 g of the substance prepared according to 2(c) in 100 ml of absolute ethanol, whilst stirring. After 6 hours, the solution was filtered in order to separate off the catalyst and the filtrate was concentrated in vacuo. 7.2 g (100% of theory) of melting point 90° C. thereby crystalline out.

(e) tert.-Butyl-adipyl-L-phenylalanine β-naphthyl ester 2.6 g of dicyclohexylcarbodiimide were added to a solution of 4.5 g of the substance obtained according to 2(d) and 1.8 g of β-naphthol in 50 ml of absolute tetrahydrofurane at 0° C. and the reaction mixture was kept at 4° C. for 15 hours. The dicyclohexylurea was separated off by filtration and the tetrahydrofurane was evaporated off from the filtrate in vacuo. The syrup thereby obtained was dissolved in a little ethyl acetate and the ethyl acetate solution was chromatographed on neutral aluminium oxide by first eluting the column with ether/petroleum ether 1:1, and then with ether, methylene chloride and methanol. On concentrating the combined ether and methylene chloride eluates, 1.8 g (30% of theory) of a syrup which crystallises under ether and has a melting point of 80° C. were obtained.

(f) Adipyl-L-phenylalanine β-naphthyl ester 10 ml of anhydrous trifluoroacetic acid were poured over 1.7 g of the tert.-butyl ester described under 2(e). After leaving the mixture to stand under nitrogen at 20° C. for one hour, the solution was concentrated in vacuo and ether was added to the syrupy residue. The ether was distilled off in vacuo and this process was repeated several times. On leaving the residue to stand under a little acetonitrile, 1.39 g (95% of theory) of colourless substance crystallised and the crystals were filtered off and washed well with ether; melting point: 94° C.

EXAMPLE 3: Succinyl-L-phenylalanine p-nitrophenyl ester (a) L-Phenylalanine p-nitrophenyl ester hydrochloride 250 ml of 5 N ethereal hydrogen chloride were added to a solution of 21 g of tert.-butoxycarbonyl-L-phenylalanine p-nitrophenyl ester in 50 ml of anhydrous tetrahydrofurane and the reaction mixture was stirred for 1 hour at 22° C., with exclusion of moisture. 250 ml of absolute ether were added to the precipitate formed and the yellowish crystals were isolated by filtration; 15.9 g (99% of theory) of melting point 191°–193° C.

(b) Succinyl-L-phenylalanine p-nitrophenyl ester 8 g (25 mmols) of the substance obtained according to 3(a) were dissolved in 150 ml of acetonitrile, with warming, and 2.5 g of succinic anhydride were added. After 30 minutes, 20 ml of water were added to the mixture at 4° C. and the pH value of the reaction solution was kept at 5.5 by adding 8 N sodium hydroxide solution. A further 2.5 g of succinic anhydride were added and the mixture was stirred at pH 5.5 for a further 1.5 hours. The crystals which had precipitated were then isolated by filtration; a further fraction was obtained on concentrating the filtrate. The combined products were recrystallised several times from acetonitrile; 6.8 g (67% of theory) of melting point 168° C.

The following Example illustrates the determination of enzymes with chymotrypsin-like specificity using succinyl-L-phenylalanine β-naphthyl ester.

EXAMPLE 4

A: Preparation of the solutions (1) 0.25 M tris buffer: 30.29 g of tris-(hydroxymethyl-)aminomethane and 0.203 g of magnesium chloride hexahydrate (analytical grade), and 0.5 g of polyethylene glycol with about 20 ethylene oxide units, etherified with lauryl alcohol, are dissolved in 700 ml of water in a 1 liter measuring flask and 1 N hydrochloric acid is added to pH 7.2. The measuring flask is then filled up to the mark.

(2) Substrate solution: 39.14 mg of succinyl-L-phenylalanine β-naphthyl ester are dissolved in 1 ml of dimethylsulphoxide. This solution can be kept in a refrigerator for a virtually unlimited period.

B: Carrying out the test (1) Blank value (determination of the spontaneous hydrolysis): 0.025 ml of substrate solution (A2) is added to 2.5 ml of the above tris buffer (A1) and the increase in extinction at 329 nm relative to a comparison solution which contains, instead of the substrate solution, the same volume of dimethylsulphoxide is measured. $\Delta_{OD}$ blank is thus determined.

(2) Test sample: tris buffer and enzyme solution (0.01–0.5 ml) are mixed such that a volume of 2.5 ml is obtained. After homogenising, 0.025 ml of substrate solution are added to the mixture and the increase in extinction at 329 nm relative to a comparison cell which contains the same amount of test solution and 0.025 ml of dimethylsulphoxide instead of the substrate solution is measured. $\Delta_{OD}$ test is obtained.

(3) Calculation of the enzyme activity: the enzymatic activity can be calculated from the values of the increase in extinction in the test solution and in the comparison or blank solution according to the following formula:

$$\text{activity } (nkat) = \frac{\Delta_{OD\ test} - \Delta_{OD\ blank}}{t \cdot 0.042}$$

In this formula, $\Delta_{OD}$ values relate to the increase in extinction in time t (in minutes) at a cell thickness of 1 (in cm).

| Enzyme | Amount used/test | Conditions | Relative rate of splitting (%) |
|---|---|---|---|
| α-Chymotrypsin | 8.5 NF U+ | pH 7.2 | 100 |
| Cathepsin D$_2$ | 1 U[1] | pH 3.0 | 0 |
| Cathepsin G | 0.50 nkat[2] | pH 7.2 | 124 |
| Elastase (granulocytes) | 0.25 nkat[3] | " | 0.5 |
| Elastase (pancreas) | 2.0 nkat[3] | " | 0.4 |
| Kallikrein (pancreas) | 4 U | " | 0 |
| Kallikrein (plasma) | 0.1 nkat[4] | " | 0 |
| Plasmin | 0.2 CU[5] | " | 0.4 |
| Thrombin | 0.05 NIH U | " | 0 |
| Trypsin | 11.5 NF U | " | 2.0 |

The Michaelis constants of α-chymotrypsin and cathepsin G and succinyl-L-phenylalanine β-naphthyl ester at 25° C. in the above 0.25 M tris-(hydroxymethyl)-aminomethane/hydrochloric acid buffer of pH 7.2 were determined as $4.2 \cdot 10^{-31\ 4}$ mol/liter and $4.5 \cdot 10^{-4}$ mol/liter respectively, by the method of H. Lineweaver and D. Burk [J. Amer. Chem. Soc. 56, 658 (1934)]. The corresponding values for the substrate adipyl-L-phenylalanine β-naphthyl ester were found to be $6.4 \cdot 10^{-4}$ mol/liter and $7.2 \cdot 10^{-4}$ mol/liter respectively.

What is claimed is:

1. A compound of the formula $$\text{HOOC—X—CONH—CH—COOY} \quad \text{(I)}$$
$$| $$
$$\text{CH}_2$$
$$|$$
$$\text{Z}$$

in which

X denotes o-phenylene, straight-chain $C_2$ to $C_4$ alkylene, straight-chain, $C_2$ to $C_4$ alkylene or $C_2$ to $C_4$ alkenylene substituted by $C_1$ to $C_4$ alkyl, Y denotes α-naphthyl, β-naphthyl, phenyl or 4-nitrophenyl and Z denotes phenyl, indolyl, or phenyl or indolyl substituted by hydroxyl.

2. A compound according to claim 1, in the L-form.

3. A compound of claim 1 which is succinyl-L-phenylalanine β-naphthyl ester.

4. A compound of claim 1 which is succinyl-L-phenylalanine 4-nitrophenyl ester.

5. A compound of claim 1 which is adipyl-L-phenylalanine β-naphthyl ester.

6. A compound of claim 1 which is adipyl-L-phenylalanine 4-nitrophenyl ester.

* * * * *

UNITED STATES PATENT AND TRADEMARK OFFICE
CERTIFICATE OF CORRECTION

PATENT NO. : 4,239,902  
DATED : December 16, 1980  
INVENTOR(S) : Eugen Schnabel et al.

Page 1 of 3

It is certified that error appears in the above—identified patent and that said Letters Patent is hereby corrected as shown below:

Column 2, line 19, "$Cm^{31}$" should be "Cm-".

Column 3, line 41, "baes" should be "bases".

Column 6, line 36, "crystalline" should be "crystallise".

Column 8, after line 7, insert the following:

"Table 1: Relative rates of splitting of succinyl-L-phenylalanine β-naphthyl ester for various proteases, measured in a 0.25 M tris-(hydroxymethyl)-amino-methane/hydrochloric acid buffer of pH 7.2, containing 0.05% Brij 35 ®.

Column 8, after the tabular data ending on line 22, insert the following:

UNITED STATES PATENT AND TRADEMARK OFFICE
CERTIFICATE OF CORRECTION

PATENT NO. : 4,239,902

DATED : December 16, 1980

INVENTOR(S) : Eugene Schnabel et al.

It is certified that error appears in the above—identified patent and that said Letters Patent is hereby corrected as shown below:

$^+$U = units; nkat = Enzyme Nomenclature, Recommendations (1972) of the International Union of Pure and Applied Chemistry and the International Union of Biochemistry, 1973, Elsevier, Amsterdam-New York, pages 26-27

1) determined using haemoglobin as the substrate, in accordance with the method of A.J.Barrett in J.T. Dingle (editor), Lysosomes, Laboratory Handbook, North Holland Publishing Co., Amsterdam-London 1972, page 123

2) determined using succinyl-L-phenylalanine β-naphthyl ester as the substrate

UNITED STATES PATENT AND TRADEMARK OFFICE
CERTIFICATE OF CORRECTION

PATENT NO. : 4,239,902

DATED : December 16, 1980

INVENTOR(S) : Eugene Schnabel et al.

It is certified that error appears in the above—identified patent and that said Letters Patent is hereby corrected as shown below:

3) determined using succinyl-L-alanyl-L-alanyl-L-alanine p-nitroanilide, in accordance with the method of J. Bieth, B. Spiess and C.G. Wermuth, Biochem. Med. $\underline{11}$, 350 (1974)

4) determined using benzoyl-L-prolyl-L-phenylalanyl-L-arginine p-nitroanilide, in accordance with the method of L.G. Svendsen, German Offenlegungsschrift (German Published Specification) 2,527,932

5) J.T. Sgouris, Vox.Sang. $\underline{5}$, 357 (1960)

Signed and Sealed this

Seventh Day of April 1981

[SEAL]

Attest:

RENE D. TEGTMEYER

Attesting Officer        Acting Commissioner of Patents and Trademarks